United States Patent [19]  [11] 4,302,598
Bellis  [45] Nov. 24, 1981

[54] RECYCLING CATALYST IN PREPARATION OF DIMETHYLFORMAMIDE FROM DIMETHYLAMINE AND CARBON MONOXIDE

[75] Inventor: Harold E. Bellis, Wilmington, Del.

[73] Assignee: E. I. Du Pont de Nemours and Company, Wilmingon, Del.

[21] Appl. No.: 217,504

[22] Filed: Dec. 17, 1980

[51] Int. Cl.$^3$ ............................................. C07C 102/00
[52] U.S. Cl. ................................................... 564/132
[58] Field of Search ........................................ 564/132

[56] References Cited

U.S. PATENT DOCUMENTS

| | | | |
|---|---|---|---|
| 1,787,438 | 1/1931 | Lacy | 564/132 |
| 2,793,211 | 5/1957 | Lo Cicero et al. | 564/132 |
| 2,866,822 | 12/1958 | Siefen et al. | 564/132 |
| 3,781,352 | 12/1973 | Hawthorne et al. | 564/132 |
| 3,922,304 | 11/1975 | Schreyer et al. | 564/132 |
| 4,098,820 | 7/1978 | Couteau et al. | 564/132 |
| 4,140,716 | 2/1979 | Malender et al. | 561/132 |

Primary Examiner—Arthur P. Demers

[57] ABSTRACT

The alkali metal methylate catalyst used in the preparation of dimethylformamide from dimethylamine and carbon monoxide can be preserved, recycled and reused if the reaction mass contains dimethylamine in excess of the stoichiometric amount at all times.

1 Claim, No Drawings

RECYCLING CATALYST IN PREPARATION OF DIMETHYLFORMAMIDE FROM DIMETHYLAMINE AND CARBON MONOXIDE

DESCRIPTION

Technical Field

This invention relates to a method for preparing dimethylformamide (DMF) from dimethyamine (DMA) and carbon monoxide, using an alkali metal methylate as a catalyst. It is more particularly directed to an improvement in that process which permits the catalyst to be recycled and reused.

BACKGROUND AND SUMMARY OF THE INVENTION

DMF is a commodity in the chemical industry, widely used as a solvent and as a reaction medium in the preparation of dyes.

One method for preparing DMF on a commercial scale is that in which DMA and carbon monoxide are catalytically reacted, using an alkali metal methylate as the catalyst. This produces crude DMF, which must be refined to be commercially acceptable. Before this is done, it is customary to remove the catalyst because its presence in the refining train together with water causes decomposition of the DMF product into DMA and formic acid, for obvious reasons an undesirable thing.

This removal is ordinarily done by adding water to the reaction mass just before it is fed to the refining train. This converts the catalyst to an alkali metal formate precipitate, as shown by the following equations:

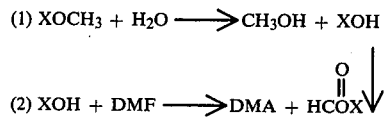

where X is an alkali metal.

As can be seen from equation (2), this procedure exacts an economic penalty because some of the product DMF is consumed. This yield loss can amount to as much as 2%, by weight. What's more, once the catalyst is so removed, it is lost and cannot be reused, which is another expense. To this must be added the additional cost of physically removing the alkali metal formate precipitate from the reaction mass.

It has now been found that the catalyst removal step is not necessary and that the catalyst can be preserved, recycled and reused if an excess of at least 0.1%, by weight, over the stoichiometric amount of DMA is present in the reaction mass at all times.

DETAILED DESCRIPTION OF THE INVENTION

The DMA-carbon monoxide reaction is run by first charging a suitable reaction vessel with DMF. To this is added 0.25-2%, by weight of the DMF of an alkali metal methylate catalyst, preferably sodium methylate. The catalyst is added as a 0.5-10%, by weight, solution in methanol.

To this catalyst-DMF mixture is then added 5-25%, by weight of the mixture, of DMA. The resulting reaction mass is then continuously stirred and its temperature is brought to and held at 20°-160° C., preferably 60°-130° C. The reactor is then pressurized to 276-1517 kPa gauge (40-220 psig), preferably 620-1379 kPa gauge (90-200 psig) with carbon monoxide.

The reaction is allowed to continue until the DMA concentration in the reaction mass is no less than about 0.1%, by weight, as determined by periodic sampling and analysis by titrating with acid. The DMA can be present in the reaction mass in an amount greater than that just stated, but this confers no additional benefit and places a burden on the process because the excess DMA must be removed in a later stage.

The reaction mass is then cooled to ambient temperature and the reaction vessel depressurized. The DMF produced by the DMA-carbon monoxide reaction is then separated from the reaction mass by distillation and is passed to a conventional refining train.

The remainder of the reaction mass containing the catalyst, after replenishment of the DMA consumed in the reaction and the methanol lost in the distillation step, can be reused in another identical reaction. For maximum efficiency, about 5-10%, by weight, of the catalyst should be replaced after each cycle because of the slight but inevitable loss in the DMF separation step and the loss due to the usual presence of small amounts of water and carbon dioxide in the reaction mass.

The DMA-carbon monoxide reaction can also be run continuously, as shown in U.S. Pat. No. 2,866,822, which is incorporated into this specification to show the details of the process.

Briefly, according to that process, DMA and a solution of methylate catalyst in methanol are introduced into a vertical reaction column at its top. The DMA and catalyst solution flow downwardly through the column, which has been pre-filled with DMA. Carbon monoxide is introduced at the bottom of the column and flows upwardly, or countercurrent to the flow of DMA and catalyst solution. Product DMF is removed from the bottom of the column.

The amounts of DMA and carbon monoxide fed into the reactor are regulated so that an excess of at least 0.1%, by weight, over the stoichiometric amount of DMA is present in the reaction zone at all times. This can be easily arranged by feeding the DMA and carbon monoxide at such rates that at least 0.1%, by weight, of DMA is continuously present in the reactor effluent.

After the DMF product has been removed from the effluent by distillation or other appropriate means, the DMF and catalyst which remain can, after replenishment as in the batch mode, be recycled to the top of the reactor.

For the process of the invention to function at maximum efficiency, it is highly desirable that the reaction mass contain no more than about 0.02-0.03%, by weight, of water.

BEST MODE

In the following description, all parts are by weight.

A reactor was charged with 140 parts of DMF, a solution of 1.8 parts of sodium methylate in 38.2 parts of methanol and 11 parts of DMA. The reactor was sealed and the contents heated to and held at 105° C., with continuous stirring. The vessel was then pressurized with carbon monoxide (1379 kPa gauge, 200 psig). These conditions were held for 40 minutes at which time the DMA content of the reaction mass was about 0.1%.

The reactor contents were then cooled to ambient temperature, the pressure released and the reactor opened. Sixteen parts of DMF and 38 parts of methanol were then distilled off at 155° C. and atmospheric pressure.

To the remainder, which contained 1.7 parts of catalyst, were added another 11 parts of DMA and 38 parts of methanol. The reaction was then repeated with substantially the same result.

I claim:

1. In the catalytic preparation of dimethylformamide from dimethylamine and carbon monoxide using an alkali metal methylate as the catalyst, the improvement which permits recycling and reuse of the catalyst, which improvement comprises the continuous presence of dimethylamine in the reaction mass at a concentration of at least 0.1%, by weight, in excess of the stoichiometric amount.

* * * * *